United States Patent
Laugharn, Jr. et al.

(10) Patent No.: US 10,398,843 B2
(45) Date of Patent: Sep. 3, 2019

(54) APPARATUS AND METHOD FOR ACOUSTIC TREATMENT AND DELIVERY OF SAMPLES FOR MEDICAL TREATMENT

(71) Applicant: Covaris, Inc., Woburn, MA (US)

(72) Inventors: James A. Laugharn, Jr., Winchester, MA (US); Carl Beckett, Harvard, MA (US); Ion A. Tsinteris, Somerville, MA (US)

(73) Assignee: Covaris, Inc., Woburn, MA (US)

( * ) Notice: Subject to any disclaimer, the term of this patent is extended or adjusted under 35 U.S.C. 154(b) by 1120 days.

(21) Appl. No.: 14/515,360

(22) Filed: Oct. 15, 2014

(65) Prior Publication Data

US 2015/0105750 A1 Apr. 16, 2015

Related U.S. Application Data

(60) Provisional application No. 61/890,894, filed on Oct. 15, 2013.

(51) Int. Cl.
*A61M 5/31* (2006.01)
*A61L 2/00* (2006.01)
(Continued)

(52) U.S. Cl.
CPC .......... *A61M 5/3134* (2013.01); *A61L 2/0011* (2013.01); *A61M 5/001* (2013.01);
(Continued)

(58) Field of Classification Search
CPC ...... A61M 5/3134; A61M 5/001; A61M 5/24; A61M 5/2448; A61M 5/3145; A61M 2005/2407; A61M 2005/247; A61L 2/0011
(Continued)

(56) References Cited

U.S. PATENT DOCUMENTS

| | | | |
|---|---|---|---|
| 1,943,120 A * | 1/1934 | Kabnick | A61M 5/2448 604/87 |
| 3,807,467 A * | 4/1974 | Tascher | A61J 1/2096 141/375 |

(Continued)

FOREIGN PATENT DOCUMENTS

WO  WO 2012061237 A1  5/2012

*Primary Examiner* — Manuel A Mendez
(74) *Attorney, Agent, or Firm* — Wolf, Greenfield & Sacks, P.C.

(57) ABSTRACT

The present disclosure relates to a vessel configured to apply pressure greater than ambient pressure and/or provide a reduced headspace to a sample, while subject to focused acoustic treatment. Such treatment may generally result in enhanced effects of sterilization and/or other processing than if the sample is otherwise treated under ambient conditions. The sample may be a medicament that is sterilized under pressure using focused acoustic energy, where the sterilized sample is subsequently delivered to a patient. A fluid delivery cartridge may include a vessel having a transfer end opposite a plunger end. The transfer end may include a sealed cover. A plunger may be movably disposed in the vessel to accommodate entry of a liquid via piercing of the sealed cover. Upon processing (e.g., sterilizing) of the sample with focused acoustic energy, the sample may be appropriately dispensed through the pierced sealed cover.

20 Claims, 10 Drawing Sheets

(51) Int. Cl.
    *A61M 5/00*         (2006.01)
    *A61M 5/24*         (2006.01)

(52) U.S. Cl.
    CPC ............ *A61M 5/24* (2013.01); *A61M 5/2448* (2013.01); *A61M 5/3145* (2013.01); *A61M 2005/2407* (2013.01); *A61M 2005/247* (2013.01)

(58) Field of Classification Search
    USPC .................................. 604/513; 53/140, 167
    See application file for complete search history.

(56) References Cited

U.S. PATENT DOCUMENTS

| | | | |
|---|---|---|---|
| 5,884,457 A * | 3/1999 | Ortiz ...................... | B65B 3/003 53/167 |
| 6,065,270 A * | 5/2000 | Reinhard ................ | B65B 3/003 53/140 |
| 6,719,449 B1 | 4/2004 | Laugharn, Jr. et al. | |
| 6,948,843 B2 | 9/2005 | Laugharn, Jr. et al. | |
| 8,353,619 B2 | 1/2013 | Laugharn, Jr. et al. | |
| 8,636,689 B2 * | 1/2014 | Halili, Jr. .............. | A61J 1/2096 604/88 |
| 8,999,704 B2 | 4/2015 | Laugharn, Jr. | |
| 2008/0031094 A1 * | 2/2008 | Laugharn, Jr. ...... | B01F 11/0283 367/138 |
| 2014/0008366 A1 * | 1/2014 | Genosar ............. | A61M 5/1782 220/265 |

* cited by examiner

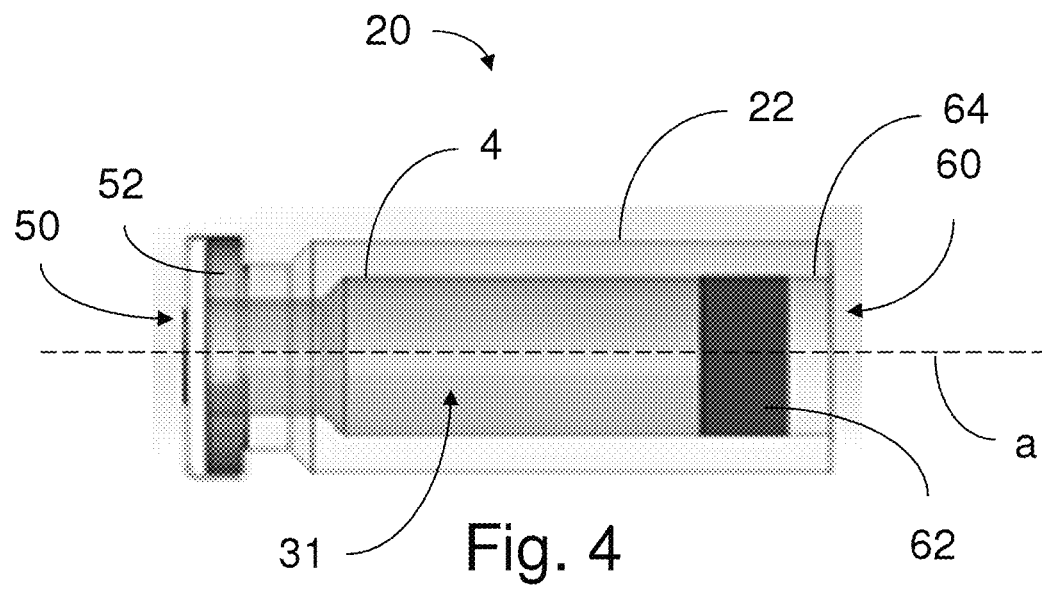
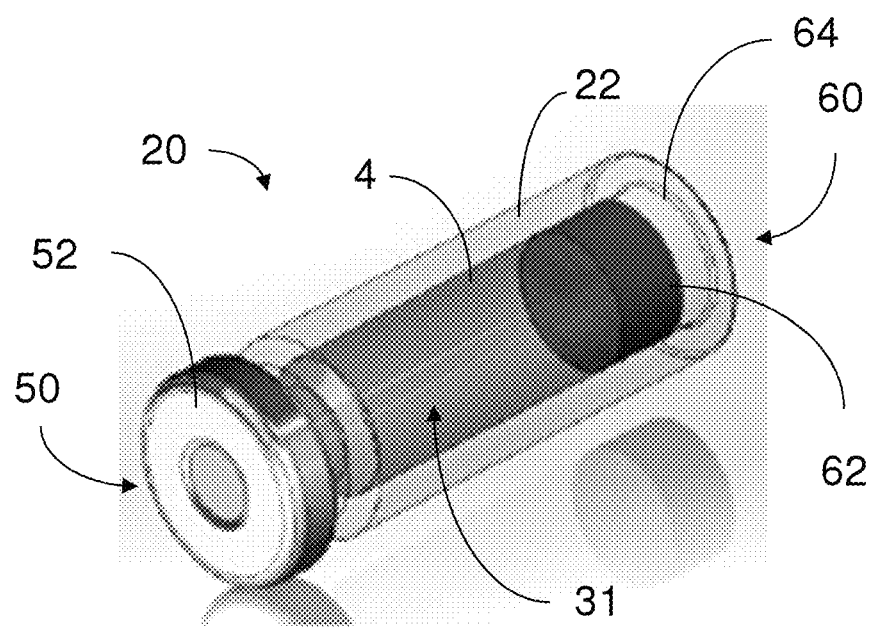

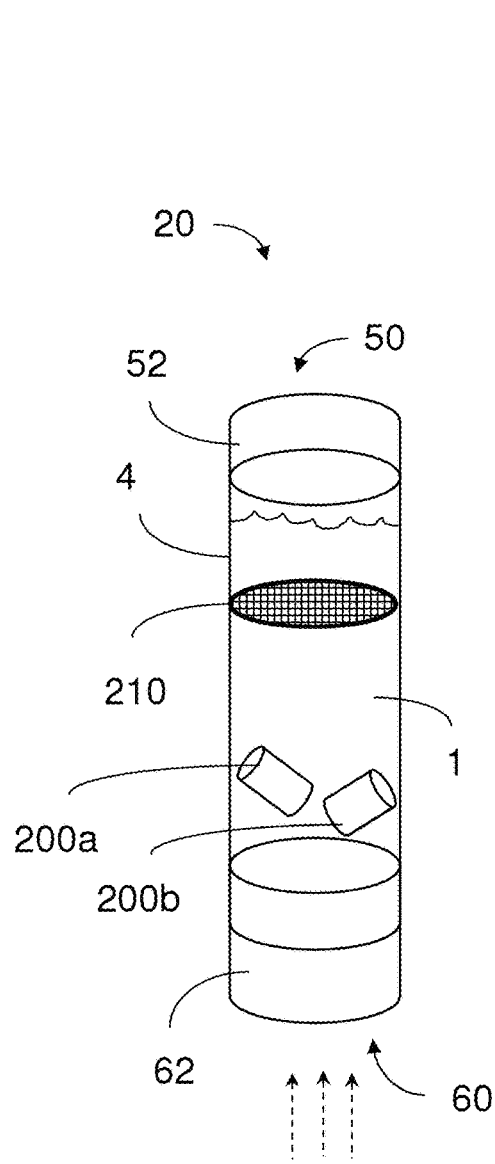
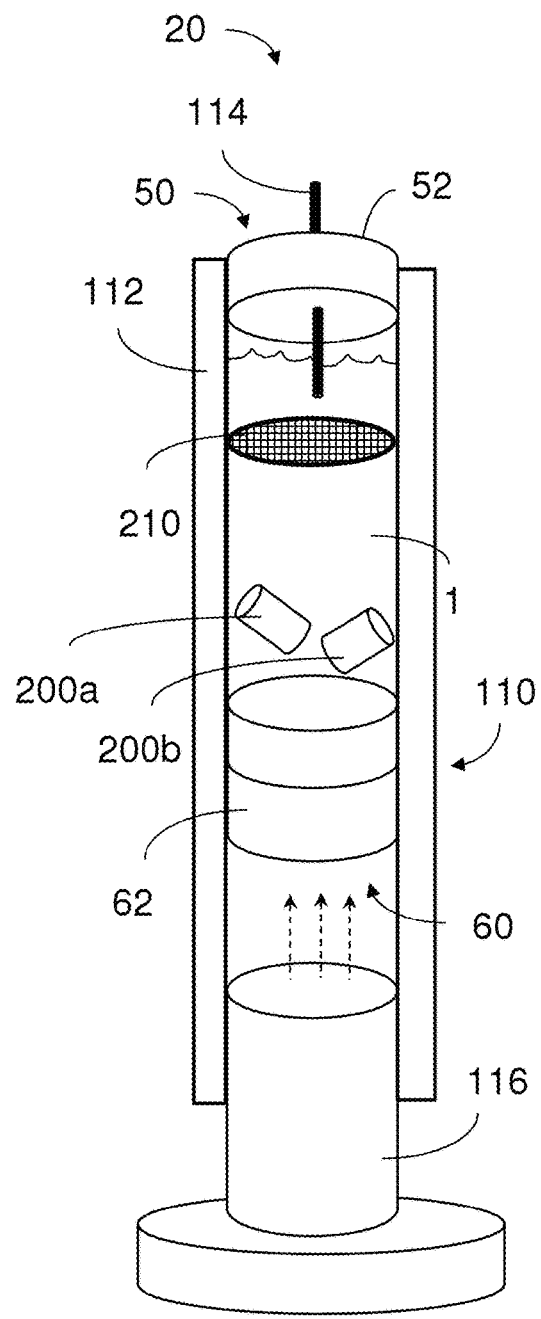
Fig. 16
Fig. 17

APPARATUS AND METHOD FOR ACOUSTIC TREATMENT AND DELIVERY OF SAMPLES FOR MEDICAL TREATMENT

BACKGROUND

Substances that are used for medical treatment, particularly those that are injected into patients, such as pharmaceuticals (e.g., drugs, steroids, antibiotics, proteins, nucleic acids) or other bioactive agents, must be adequately sterilized. If not properly sterilized, such substances may pose serious risks for infection or exposure of other harmful disease(s) to the general population. For instance, recently, contaminated steroid shots given to a large portion of the population has led to an outbreak of fungal meningitis, resulting in the sickness and deaths of numerous people.

Acoustic energy-based sample processing devices, such as Adaptive Focused Acoustic apparatuses made by Covaris of Woburn, Mass., are effective for homogenization and disruption of biological tissues, cells and other sample material. The devices are also beneficial for chemical applications, such as compound dissolution, formulation, micronization, emulsification and other processes.

SUMMARY

Pharmaceutical formulations that may be at risk for contamination, yet are injected into the body, must be properly sterilized; otherwise, the chances for disease to uncontrollably spread are vastly increased. The inventors have recognized that focused acoustic processing may be advantageous for effectively sterilizing such samples (e.g., pharmaceutical formulations) or otherwise enabling the sterile preparation of samples that are used for medical treatment. The inventors have further appreciated that certain conditions exist where focused acoustic processing may be particularly beneficial in sterilizing these samples and/or resulting in a desired effect (e.g., enhanced reaction yield(s), providing more controlled processing conditions, improving formulations).

For instance, subjecting samples held within a vessel to focused acoustic treatment while under a pressure greater than that of the ambient environment may result in a higher power treatment and, thus, more effective sterilization and/or other processing effect than if the samples were treated at ambient pressure. When focused acoustic energy is applied to a sample while under high pressure, in some cases, the desired result may be obtained in a shorter period of time and/or may result in improved output quality (e.g., greater degree of sterilization of the sample, enhanced reaction/formulation output). In certain embodiments, an air-tight seal is formed between the interior space of the vessel (e.g., by attachment of one or more sealed covers or other sealing material at an entrance) to permit pressurization of the interior space of the vessel relative to the surrounding atmosphere. Various systems and methods for pressurizing an interior space of a vessel are described in U.S. Publication No. US2008/0031094, entitled "Methods and apparatus for treating samples with acoustic energy," which may be used in association with aspects of the present disclosure. In addition, other techniques and systems are described herein for pressurizing a sample volume during acoustic treatment.

Focused acoustic treatment of a sample in a vessel that has a reduced headspace above the sample may also be effective for purposes of sterilizing the sample. A reduced headspace may increase the time of exposure of the sample to an acoustic focal zone so as to enable higher acoustic doses to be delivered to the sample. In some embodiments, the volume of gas contained in the vessel is less than about 10% of the volume of the sample (e.g., liquid) contained in the vessel. In some cases, reduction or control of the headspace may in some arrangements provide the ability to reduce or eliminate ejection or other movement of sample material from a desired region in a vessel, may provide for more efficient transmission or use of acoustic energy in the sample material, or may provide other advantages. Various systems and methods of headspace control are described in U.S. application Ser. No. 13/186,858, entitled "Method and Apparatus for Headspace Control in Acoustic Processing of Samples," which also may be used in association with aspects of the present disclosure. In addition, other techniques and systems are described herein for controlling a headspace in a sample volume during acoustic treatment.

The inventors recognize that the incorporation of overpressure and/or reduced headspace used in combination with focused acoustic treatment for processing samples, for example, sterilizing samples used for medical treatment, may result in a higher power and more efficient results than if the adjustments to pressure and/or headspace are absent. Various embodiments of the present disclosure provide for an improved cartridge-type system that allows for suitable focused acoustic processing and handling of the sample to occur, with desirable results, in a convenient, efficient manner.

When sterilizing, once the sample is adequately sterilized, the sample must remain sterile, without risk of contamination, upon injection into a patient. The inventors have developed a system and device where a sample may be transferred to a vessel, sterilized or otherwise processed in sterile conditions under focused acoustics, and delivered to a patient without exposure of the sample to the exterior environment that surrounds the vessel and the treatment chamber.

In an illustrative embodiment, a method for using a fluid delivery cartridge is provided. The method includes providing a fluid delivery cartridge having a vessel with a transfer end opposite a plunger end. The transfer end includes a sealed cover that is pierceable. The vessel also has a plunger movably disposed in the vessel and located adjacent the sealed cover. The method further includes providing a liquid into the vessel by piercing the sealed cover and passing the liquid through the sealed cover and into the vessel. The plunger is moved in the vessel in a direction away from the sealed cover and toward the plunger end to accommodate liquid provided into the vessel.

In another illustrative embodiment, a fluid delivery cartridge is provided. The fluid delivery cartridge includes a vessel having a transfer end opposite a plunger end; a sealed cover (e.g., crimp cap with a pierceable membrane, pierceable plug composed of a resilient material, rubber stopper) that is pierceable attached at the transfer end; and a plunger movably disposed in the vessel and located adjacent the sealed cover. The plunger is arranged for movement in the vessel in a direction away from the sealed cover and toward the plunger end with introduction of liquid into the vessel. The cartridge is further arranged for association with a focused acoustic treatment system and exposure to focused acoustic energy to sterilize liquid in the vessel.

In yet another illustrative embodiment, a fluid delivery cartridge is provided. The fluid delivery cartridge includes a vessel having a transfer end opposite a plunger end; a sealed cover that is pierceable attached at the transfer end; and a plunger movably disposed in the vessel and located adjacent the sealed cover. The plunger is arranged for movement in the vessel in a direction away from the sealed cap and toward the plunger end with introduction of liquid into the vessel. The cartridge is also arranged to receive a liquid under pressure via a needle that pierces the sealed cover. The plunger is arranged to move in the vessel in a direction away from the sealed cover in response to pressurized liquid introduced into the vessel.

In a different illustrative embodiment, a fluid delivery cartridge is provided. The fluid delivery cartridge includes a vessel having a transfer end opposite a plunger end; a sealed cover that is pierceable attached at the transfer end; and a plunger movably disposed in the vessel and located adjacent the sealed cover. The plunger is arranged for movement in the vessel in a direction away from the sealed cover and toward the plunger end with introduction of liquid into the vessel. The cartridge is arranged for association with a focused acoustic treatment system that applies force to the plunger to move the plunger toward the transfer end and apply pressure to liquid in the vessel before or during acoustic treatment.

In another illustrative embodiment, a method for processing a drug in a fluid delivery cartridge is provided. The method includes providing a fluid delivery cartridge having a vessel with a transfer end opposite a plunger end. The transfer end includes a sealed cover that is pierceable and the vessel has a payload including a liquid component and a plunger movably disposed in the vessel. The fluid delivery cartridge is exposed to focused acoustic energy to process the payload. Processing of the payload includes exposing the payload to acoustic energy suitable to at least mix or sterilize the payload. The acoustic energy-processed payload is dispensed from the fluid delivery cartridge for delivery to a subject by piercing the sealed cover and moving the plunger toward the transfer end to force the payload from the vessel.

The acoustic energy may be arranged in any suitable way, e.g., defining a focal zone that at least partially overlaps the sample and is sufficient to cause at least one of lysing, extraction, permeabilizing, stirring, catalyzing, degrading, fluidization, heating, particle breakdown, nucleic acid shearing, sterilization, or disruption of molecular bonds in the sample. In some embodiments, the acoustic energy source is spaced from and exterior to the vessel so that at least a portion of the acoustic energy propagates exterior to the vessel, and the acoustic energy comprises a frequency of between about 100 kilohertz and about 100 megahertz and a focal zone having a width of less than about 2 centimeters.

Other advantages and novel features of the present disclosure will become apparent from the following detailed description of various non-limiting embodiments when considered in conjunction with the accompanying figures and claims.

BRIEF DESCRIPTION OF THE DRAWINGS

Aspects of the present disclosure are described with reference to illustrative embodiments shown in the drawings, in which like numerals reference like elements, and wherein:

FIG. 4 depicts a plan view of another fluid delivery cartridge in accordance with some embodiments;

FIG. 5 illustrates a perspective view of the fluid delivery cartridge of FIG. 4;

FIGS. 14-17 show process steps for mixing a solid and liquid within a fluid delivery cartridge in accordance with some embodiments;

DETAILED DESCRIPTION

Figure 1:
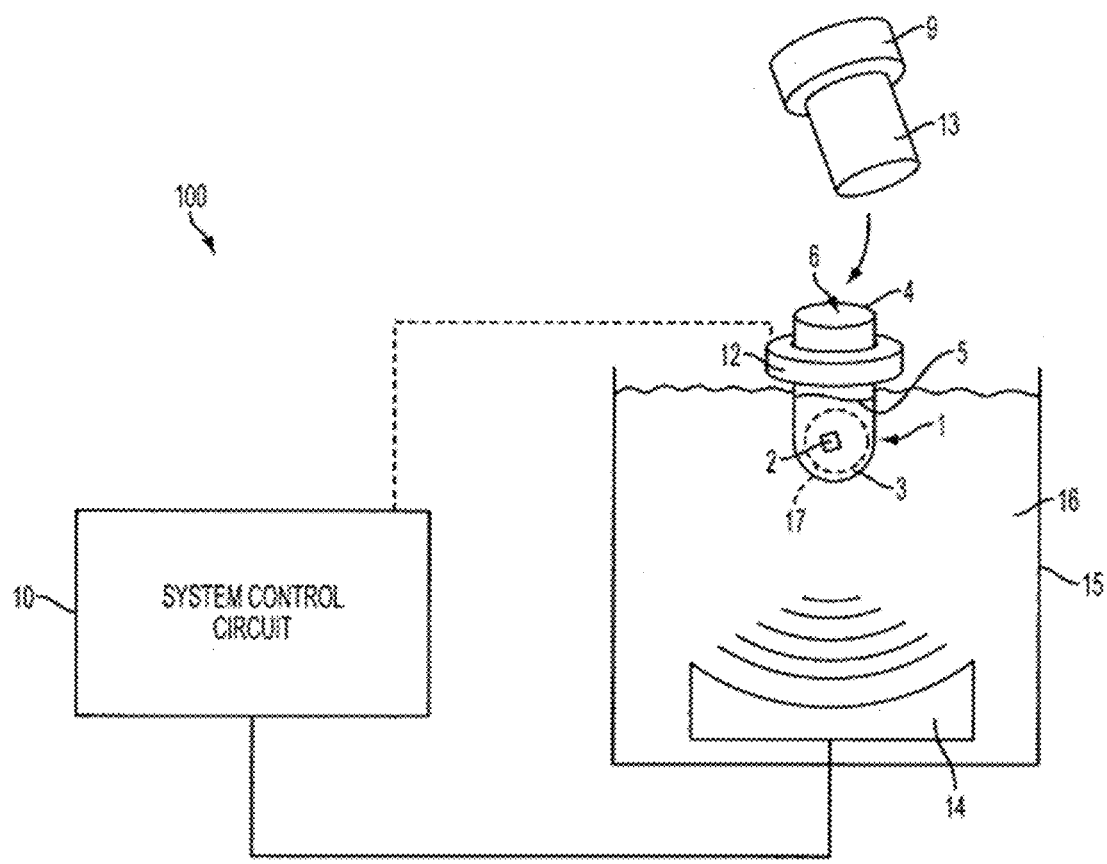
FIG. 1 shows a schematic block diagram of an acoustic treatment system that incorporates one or more aspects of the present disclosure.

Aspects of the present disclosure and embodiments described are not limited in application to the details of construction and the arrangement of components set forth in the following description or illustrated in the drawings. Other embodiments may be employed and may be practiced or carried out in various ways. Also, aspects of the present disclosure may be used alone or in any suitable combination with each other. Thus, the phraseology and terminology used herein is for the purpose of description and should not be regarded as limiting.

As described above, acoustic treatment systems can be useful for sterilization of samples and disruption of biological tissues, cells and other sample material, with the end goal of eradicating contamination of substances used for medical treatment (e.g., pharmaceuticals for injection into the body) and eliminating unnecessary risks of disease. Examples of such acoustic treatment systems and control arrangements are described in U.S. Pat. Nos. 6,948,843 and 6,719,449, assigned to Covaris of Woburn, Mass.

The conditions under which samples are subject to focused acoustic processing may contribute to the overall efficacy of the acoustic treatment. For example, processing a sample with focused acoustics under a pressure that is substantially greater than that of the surrounding environment may result in a greater degree of sterilization of the sample if the pressure difference were absent. In some embodiments, a sample to be sterilized under focused acoustics is placed within an interior space of a vessel that is pressurized to a pressure substantially greater than that of the surrounding environment. For example, if the pressure of the surrounding environment is 1 atm, then the pressure of the interior space of the vessel may be increased to a pressure, or pressure above that of the surrounding environment, of between 1 atm and about 10 atm, between about 2 atm and about 8 atm, or between about 3 and about 6 atm.

In addition to an overpressure within the interior space of the vessel, a reduced headspace above the sample may also be effective for enhancing sterilization of the sample subject to focused acoustic processing. In some embodiments, the headspace above the sample within the interior space of the vessel may be 50% or less of the sample volume. In some embodiments, the headspace may be 20% or less of the sample volume, 10% or less of the sample volume, 5% or less of the sample volume, 3% or less of the sample volume, 2% or less of the sample volume, 1% or less of the sample volume, or, e.g., as low as 0% of the sample volume.

Accordingly, combined conditions of overpressure and reduced headspace within the interior space of the vessel may provide for both higher power and more efficient treatment of the sample than if the pressure and/or headspace conditions are absent.

FIG. 1 shows a schematic block diagram of an acoustic treatment system 100 that incorporates one or more aspects of the present disclosure. It should be understood that although embodiments described herein may include most or all aspects of the present disclosure, aspects of the present disclosure may be used alone or in any suitable combination with other aspects of the present disclosure. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. In this embodiment, the vessel 4 is a standard rimless 13×100 mm borosilicate glass test tube, but it should be understood that the vessel 4 may have any suitable shape, size, material, or other feature. For example, the vessel 4 may be a cylindrical tube with a flat bottom and a threaded top end to receive a cap 9, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes. The vessel 4 may have an interior space that is suitable to accommodate an overpressure, i.e., a pressurized state where the pressure within the interior space is greater than the pressure of the environment exterior to the vessel. Other embodiments of the vessel 4 are described herein, for example, a vessel having a transfer end opposite a plunger end incorporated with a fluid delivery cartridge, as discussed in more detail further below for various illustrative embodiments. The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silica material), which is also attached to a vessel holder 12, which may be formed, at least in part, by an opening or other feature of the medium 16. Thus, the transducer 14, medium 16 and holder 12 may be formed as a single integrated part, if desired. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. In addition, or alternatively, the transducer 14 may form the focal zone 17 so that the focal zone 17 is suitably positioned relative to the sample 1 or vessel 4.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

In this illustrative embodiment, the sample 1 includes a solid material 2 and a liquid 3, e.g., 100 milligrams of a biological sample material in 1 milliliter of distilled water. Of course, those of skill in the art will appreciate that the sample 1 is not limited to a solid material 2 in a liquid 3, as the sample 1 may take any suitable form, such as a liquid only form, a solid only form, a mixture of liquid and solid as in this embodiment, a gel, a semi-solid, a gas, and/or combinations thereof. Samples may include any suitable material(s), such as biological materials (e.g., proteins, liposomes, nucleic acids, antibiotics, steroids, bioactive agents, etc.).

An interface 5 separates the sample 1 from the headspace 6, which is shown to be a gaseous region immediately above the sample 1. For some power levels at the focal zone 17 and/or sample types or arrangements, acoustic energy suitable to cause mixing, e.g., lysing, extraction, permeabilizing, catalyzing, degrading, fluidization, heating, particle breakdown, sterilization, shearing and/or disruption of molecular bonds in the sample 1, may also cause portions of the sample 1 (including solid material 2 and/or liquid material 3 of the sample 1) to be splashed or otherwise ejected from the interface 5. In some cases, the ejected sample 1 may return to the main volume of sample 1, but in other cases, the ejected sample 1 may adhere to the vessel 4 above the interface 5 or otherwise fail to return to the main sample 1. In either case, the ejected sample 1 may spend a reduced amount of time in the focal zone 17.

In addition, or alternatively, acoustic energy may cause gas in the headspace 6 to be entrained into the sample 1, such as by dissolving a portion of the gas in the headspace 6 and/or by capturing bubbles of headspace gas in the sample due to motion of the liquid at the interface 5. As discussed above, gas in the sample 1 may interfere with acoustic energy, such as by gas bubbles at or near the focal zone 17 reflecting acoustic energy away from the sample 1 and/or by dissolved gas increasing a pressure in cavitation bubbles created by acoustic energy, thereby decreasing the rate or force at which the cavitation bubbles collapse. The inventor believes that the collapse of cavitation bubbles transfers significant kinetic energy to sample materials, causing the materials to be lysed, sheared or otherwise mechanically operated on. By increasing a pressure in such bubbles, dissolved gas in the sample can reduce the energy released by cavitation bubble collapse, reducing an effectiveness of acoustic treatment.

In accordance with an aspect of the present disclosure, a headspace at an interface of a sample can be controlled, e.g., in volume and/or surface area presented at the interface, to reduce an amount of gas available for entrainment in the sample. Headspace size (volume and/or surface area presented at the interface 5) can be controlled in a variety of different ways. For example, a cap 9 may be engaged with the vessel 4 so as to position a headspace control member 13 near the interface 5. In this embodiment, the headspace control member 13 is attached to the cap 9 (e.g., formed as a unitary part with the cap 9), but other arrangements are possible as discussed more below. The headspace control member 13 may reduce a volume of the headspace 6 to be 50% or less (e.g., 20% or less, 10% or less, 5% or less, 2% or less, 1% or less) than the volume of the sample. In some embodiments, the volume of the headspace 6 may be 10% or less than the volume of the sample 1, even as little as 0% of the sample volume where the headspace control member 13 is in contact with the sample 1 at the interface 5.

Figure 2:
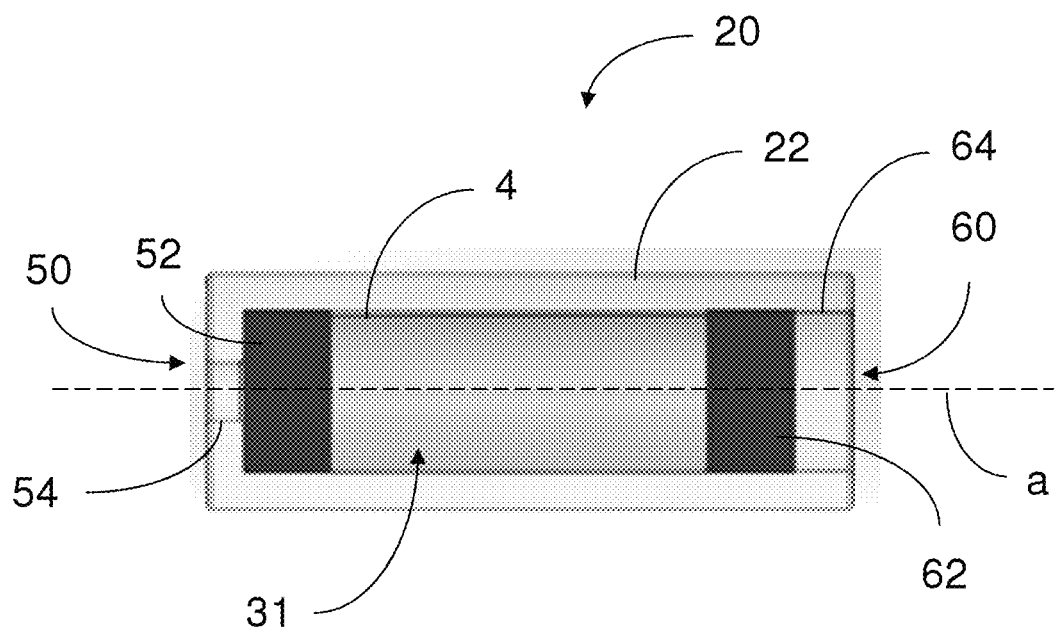
FIG. 2 depicts a plan view of a fluid delivery cartridge in accordance with some embodiments.
Figure 3:
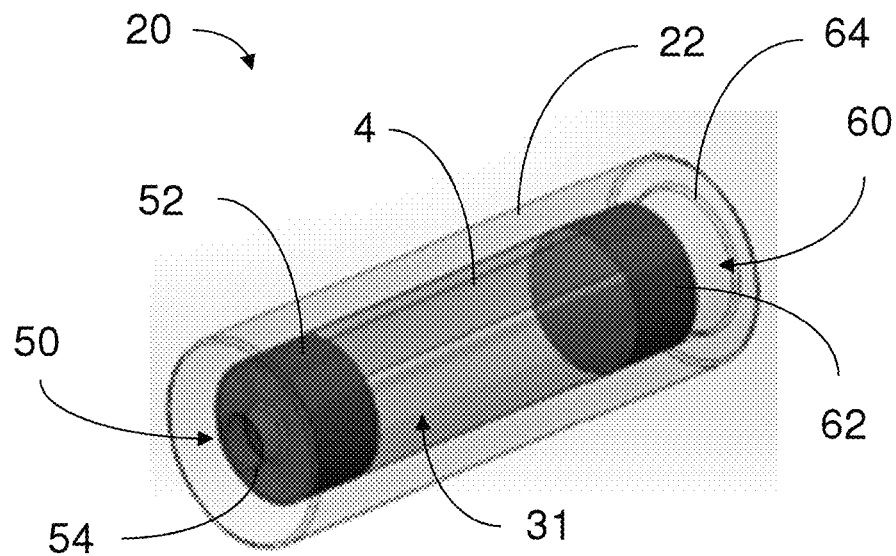
FIG. 3 illustrates a perspective view of the fluid delivery cartridge of FIG. 2.

In another aspect of the present disclosure, a fluid delivery cartridge may be arranged to receive and/or hold a sample for both acoustic treatment (e.g., for sterilization, mixing, etc.) and for use in delivering the sample to a subject (e.g., via a syringe or other device that uses the cartridge). FIGS. 2 and 3 show an illustrative embodiment of a fluid delivery cartridge 20 having a vessel 4 that includes a housing 22 that surrounds an interior space 31 of the vessel. The vessel 4 may be any suitable shape, such as a cylinder having a circular cross section; or vessel having an ellipsoidal or oblong cross section. Alternatively, the vessel 4 may have a polyhedral shape (e.g., rectangular prism, cuboid, etc.). The cartridge includes a transfer end 50 and a plunger end 60 disposed opposite one another.

A cover 52 that is pierceable may be attached to the cartridge and provide a seal at the transfer end 50. In this embodiment, the sealed cover 52 is a pierceable plug made of a resilient material, such as a rubber stopper. Accordingly, a needle (not shown) may enter through a channel 54 of the cartridge and pierce the sealed cover 52 so that a sample (e.g., pharmaceutical formulation contemplated for injection into a patient) may be introduced through the needle into the interior space 31 of the vessel 4. As mentioned above, the cover is composed of a resilient material such that upon withdrawal of the needle from the cover 52, the seal between the interior space 31 of the vessel and the exterior environment is maintained. In some embodiments, the cover 52 includes a headspace control member that depends down (e.g., movable toward) into the interior space of the vessel so as to reduce the amount of headspace that would otherwise be present when the sample is inside the vessel.

A plunger 62 may be positioned at the plunger end 60 or at another location in the vessel 22. In some embodiments, the plunger 62 is movable with respect to the vessel 4 in directions toward and away from the transfer end. Or, as shown in FIGS. 2-5, the plunger is constructed to move through a channel 64 in either direction along a longitudinal axis a defined by the vessel. Accordingly, when a sample (e.g., fluid, powder, solution, liquid, gas) is introduced into the vessel 4 from the transfer end 50, to accommodate the added material/volume within the interior space 31, the plunger 62 may be constructed to move in a direction away from the transfer end 50 and toward the plunger end 60.

In some embodiments, the plunger 62 may be initially located adjacent the sealed cover 52 so that when a liquid under pressure is introduced into the interior space 31 of the vessel 4 through the sealed cover 52, the plunger 62 may move relative to the vessel in a direction away from the transfer end 50 in response to the pressurized liquid introduced into the vessel. Alternatively, or in addition, an external force may be applied to the plunger 62 that urges the plunger 62 to move toward the transfer end 50 so as to apply pressure to the sample in the vessel. For example, a person, or mechanical assist device, may push the plunger 62 toward the transfer end 50. By decreasing the volume of the interior space 31 of the vessel 4 or otherwise urging the plunger 62 toward the transfer end, the pressure within the interior space increases; hence, the sample is subject to an overpressure within the vessel as compared to the existing pressure of the surrounding environment. As noted above, this overpressure condition may be useful during acoustic processing.

FIGS. 4 and 5 depict another embodiment of a fluid delivery cartridge 20 including a vessel 4 with a housing 22 surrounding an interior space 31. The plunger end 60 of the cartridge of FIGS. 4-5 including a plunger 62 and a channel 64 through which the plunger may move back and forth is substantially similar to the plunger end of the cartridge shown in FIGS. 2-3. The sealed cover 52 attached to the cartridge at the transfer end 50 is also pierceable.

Though, in this embodiment, the sealed cover 52 includes a cap crimped to the vessel at the transfer end 50 and a pierceable membrane positioned between the crimped cap and the vessel. Accordingly, a needle may enter through a channel 54 and pierce the membrane of the sealed cover 52 for the sample to be introduced into the interior volume of the vessel 4. Similar to the previous embodiment, when the needle is withdrawn from the cover 52, the interior space 31 of the vessel remains sealed off and isolated from the exterior environment. In various embodiments, the cover may also include a headspace control member (not shown in the figures).

Figure 6:
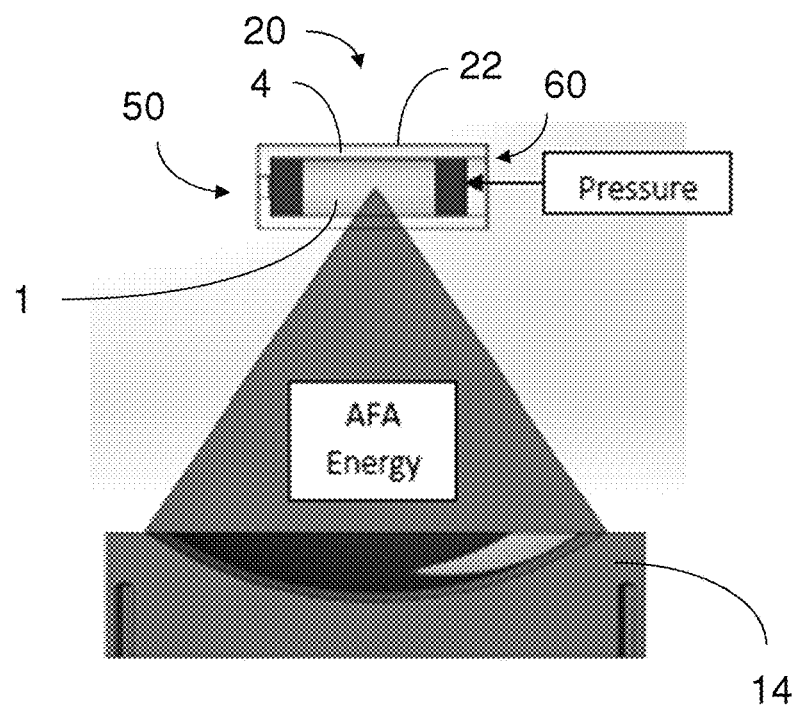
FIG. 6 shows a schematic of the fluid delivery cartridge of FIG. 2 being treated with focused acoustic energy in accordance with some embodiments.

The cartridge 20 may be suitably arranged for processing by a focused acoustic treatment system where a sample contained within the vessel is sterilized or otherwise processed due to exposure to an appropriate level of focused acoustic energy. FIG. 6 shows the cartridge 20 positioned in a manner such that the sample (not expressly shown in this figure) within the vessel 4 is subject to focused acoustic energy generated from a transducer 14.

In some embodiments, while the sample is being processed under focused acoustics, the interior space of the vessel is simultaneously under a pressure that is greater than the ambient pressure surrounding the vessel. As discussed previously, this increased pressure within the interior space of the vessel may enhance the effects of the focused acoustic processing, for example, the effective power and efficiency of the treatment may be greater due to the overpressure. For example, the increased pressure may result in an overall improvement in the sterilization effect of focused acoustic energy treatment of the sample within the vessel.

In some embodiments, to apply pressure, the plunger 62 of the cartridge is moved or otherwise urged to move toward the transfer end 50, resulting in an increase in pressure within the vessel; thus, in this environment, the sample is pressurized. Such pressure may be applied to the sample before or during focused acoustic processing. For example, as soon as focused acoustic processing begins, the plunger 62 may be urged toward the transfer end 50 of the vessel increasing the pressure within the interior space of the vessel. Or, even before focused acoustic processing occurs, the plunger 62 may be forced toward the transfer end 50 so as to pressurize the sample. As processing continues, the plunger 62 may be kept in its position so as to maintain the pressure within the interior space of the vessel during treatment. In some cases, during focused acoustic processing, the position of the plunger 62 may be suitably adjusted so as to control the degree of overpressure to which the sample is exposed. In some embodiments, the headspace above the sample within the interior space of the vessel may also be reduced so as to enhance the sterilizing effects of the focused acoustic treatment.

Figure 7:
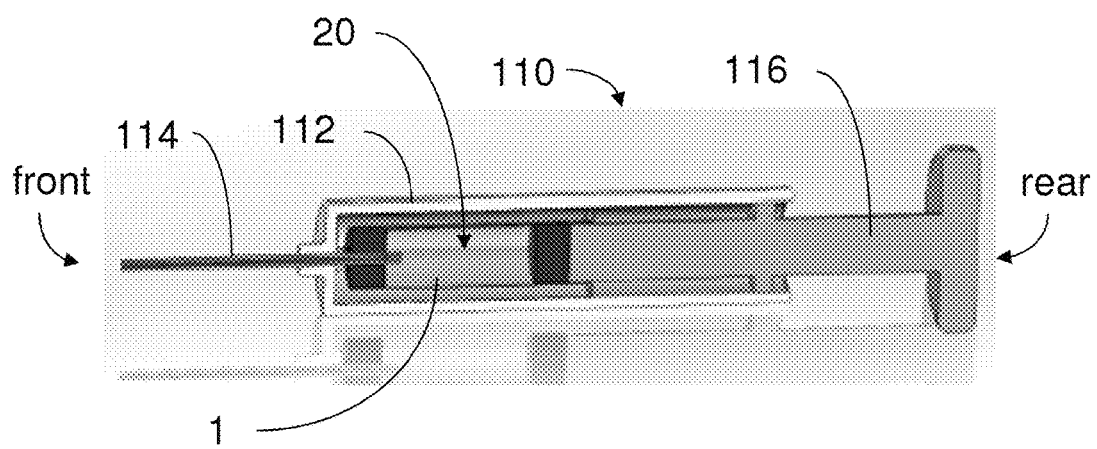
FIG. 7 depicts a plan view of the treated fluid delivery cartridge of FIG. 6 placed in a suitable syringe in accordance with some embodiments.

Once focused acoustic processing of the sample is finished and the sample is adequately sterilized or otherwise processed, the sample may be ready for injection into or other delivery to a patient. Accordingly, the cartridge 20 may be used in association with an appropriate treatment device so that the sample may be ejected from the vessel. FIG. 7 shows an illustrative embodiment of a syringe 110 having a chamber 112 within which the cartridge may be placed.

The syringe 110 also includes a needle 114 and a plunger 116 that are constructed to appropriately engage with the cartridge. For instance, before the cartridge 20 is placed within the chamber 112, the plunger 116 may be removed from the chamber 112 making room for insertion of the cartridge 20 through the rear of the syringe. Once the cartridge 20 is appropriately situated, the plunger 116 may be inserted behind the cartridge.

Further, the cartridge may be positioned such that a rear end of the needle 114 is inserted through the cover 52 and into the interior space of the vessel, providing a pathway for the sample to be transferred out from the cartridge and, for example, ultimately into a patient. Accordingly, the plunger 116 may be used to push the plunger 62 of the cartridge toward the transfer end 50 so that the sample enters into the rear end of the needle 114 and exits out the front end. To maintain sterilization of the sample, all parts of the syringe 110 are appropriately sterilized and packaged prior to use.

Though, in some embodiments, sterilized samples within a cartridge are not immediately placed into a syringe or other treatment medium. Accordingly, once the samples are sterilized or otherwise processed under focused acoustic processing (e.g., while also subject to an overpressure and/or reduced head space), the samples may be appropriately packaged and stored (e.g., in an inert gas atmosphere, freeze dried, etc.) for use at a future time. For instance, the cartridge itself, containing the sterilized samples, may be appropriately stored so that the sterilized samples may be accessed when needed. Or, the sterilized samples may be transferred to another container, maintaining its sterility, and subsequently stored for later use.

Figures 8, 9, 10:
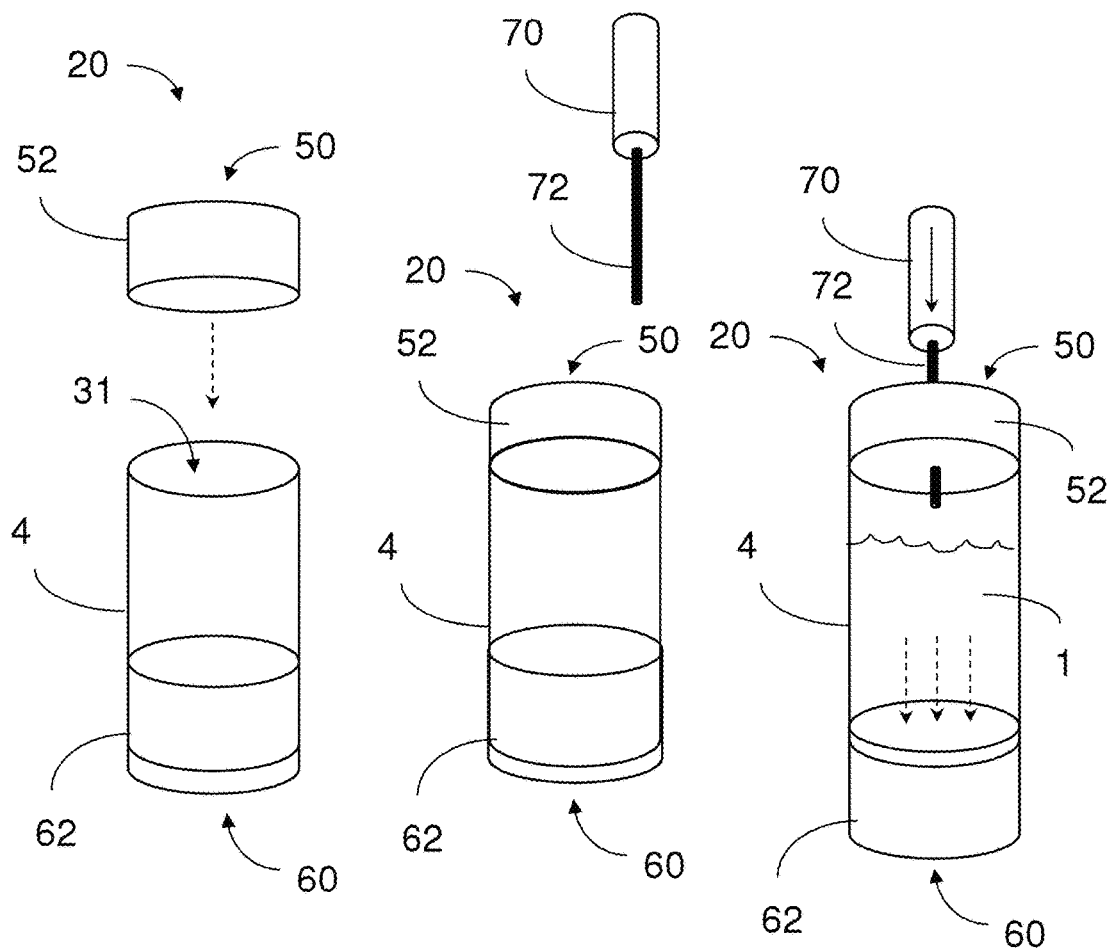
FIGS. 8-13 show process steps for delivery of fluid into a cartridge, treatment and placement in a suitable syringe in accordance with some embodiments.

FIGS. 8-13 depict an illustrative embodiment of a process where the fluid delivery cartridge 20 is used to sterilize a sample for subsequent medical treatment. An air-tight seal is formed at the plunger end 60. FIGS. 8 and 9 show a cover 52 being placed at the transfer end 50 of the cartridge so as to form another air-tight seal between the interior space 31 and the exterior environment surrounding the cartridge. Accordingly, both the transfer end 50 and the plunger end 60 of the vessel 4 are hermetically sealed isolating the interior space 31 from the exterior environment (e.g., preventing migration air, fluid, liquid, gas between the interior space and the exterior of the cartridge).

In some embodiments, the interior space 31 of the vessel 4 is pre-pressurized before the sample is placed within the interior space. For example, once the cover 52 is suitably attached at the transfer end 50 so as to form a seal, an inert gas (e.g., nitrogen, argon, helium, etc.) may be injected into the interior space of the vessel to reach a pressure that is greater that the pressure of the surrounding environment. In some embodiments (not shown in the figures), a valved conduit may be provided as a passageway for an inert gas to be flooded into the interior space 31 in a controlled manner. Or, a septum at one of the ends 50, 60 may be pierced so as to allow the interior space 31 to be pressurized without exposure to the surrounding environment.

A pressurizing atmosphere may include, for example, compressed air, nitrogen, argon, helium, or any other suitable gases or combination thereof. Certain gases may be preferred in certain applications, e.g., for their intrinsic physical properties such as inhibiting biological events, such as nitrogen, or because they may beneficially alter the cavitation threshold energy, such that an altered headspace over a fluidic or partially fluidic/solid sample more readily enables bubble formation and collapse.

FIG. 9 depicts a transfer device 70 having a needle 72 for injecting a fluid sample (e.g., liquid, gas) into the interior space 31 of the vessel. In FIG. 10, the needle 72 has pierced the sealed cover 52, allowing fluid sample to enter into the cartridge by passing through the sealed cover and into the vessel.

As discussed above, the plunger 62 located at the plunger end 60 of the cartridge may be movable (e.g., slidable) in a direction toward or away from the transfer end 50. To accommodate entry of the liquid sample into the vessel, the plunger 62 moves in a direction away from the sealed cover toward the plunger end 60, as shown by the dashed arrows in FIG. 10. Movement of the plunger in this manner avoids any need to exhaust any fluid (e.g., liquid, air, gas) from the cartridge during the step of filling. In some embodiments, the plunger 62 may be initially positioned adjacent the cover 52 at the transfer end 50, and liquid that is under pressure (e.g., pressurized liquid) may be provided into the vessel in a manner that results in movement of the plunger 62 away from the transfer end 50 and toward the plunger end 60. In some embodiments, the vessel 4 may contain a powder (such as a dry medicament) that has an enhanced ability to remain sterile for long periods as compared to a liquid solution containing the medicament. Addition of liquid to the vessel, e.g., as shown in FIGS. 9 and 10, may provide a solute to dissolve the medicament and make a sample ready for delivery to a subject. Acoustic processing may help mix the powder and liquid together, as needed.

Other components of a sample may be provided in a vessel 4 and subjected to acoustic processing to form a sample having characteristics needed for use in treating a subject. For example, components for making a set of liposomes or other structures may be provided in a vessel which is then subjected to acoustic treatment to form the desired liposomes or other structures in the vessel. In another example, components for forming desired crystalline structures may be provided to a vessel, and then acoustically processed to form the crystalline structures, e.g., relatively large crystal materials may be broken down in to smaller nanocrystals of a desired size range found optimal for medical treatment. Other examples are possible, as the processes for acoustic treatment may have a variety of different effects on a sample.

Sample delivery into the cartridge together with suitable plunger movement may provide for a suitable amount of headspace above the liquid-gas interface within the interior space of the vessel, that is, the difference between the volume of gas compared with the volume of liquid within the interior space of the vessel. As further described herein, reduction of headspace during focused acoustic treatment may also enhance sterilization or other processing effects of the sample.

In some embodiments, the volume of gas within the interior space of the vessel is less than about 50% (e.g., less than about 40%, less than about 30%, less than about 20%, less than about 15%, less than about 10%, less than about 5%, less than about 2%, or less than about 1%) of the volume of liquid within the interior space of the vessel. In some embodiments, the volume of gas within the interior space of the vessel is between about 0% and about 50% (e.g., between about 1% and about 40%, between about 1% and about 30%, between about 1% and about 20%, between about 1% and about 15%, between about 1% and about 10%, between about 1% and about 5%, or between about 1% and about 2%) of the volume of liquid within the interior space of the vessel.

A suitable volume of liquid sample to be sterilized via focused acoustics may be delivered into the interior space of the vessel. In some embodiments, the volume of liquid sample delivered into the interior space of the vessel is less than about 5 mL, less than about 3 mL, less than about 2 mL, less than about 1 mL, or less than about 0.5 mL. For example, the volume of liquid sample delivered into the interior space of the vessel may be between 0 mL and about 5 mL, between about 0.1 mL and about 3 mL, between about 0.5 mL and about 2 mL, or between about 0.5 mL and about 1 mL.

Figures 11, 12, 13:
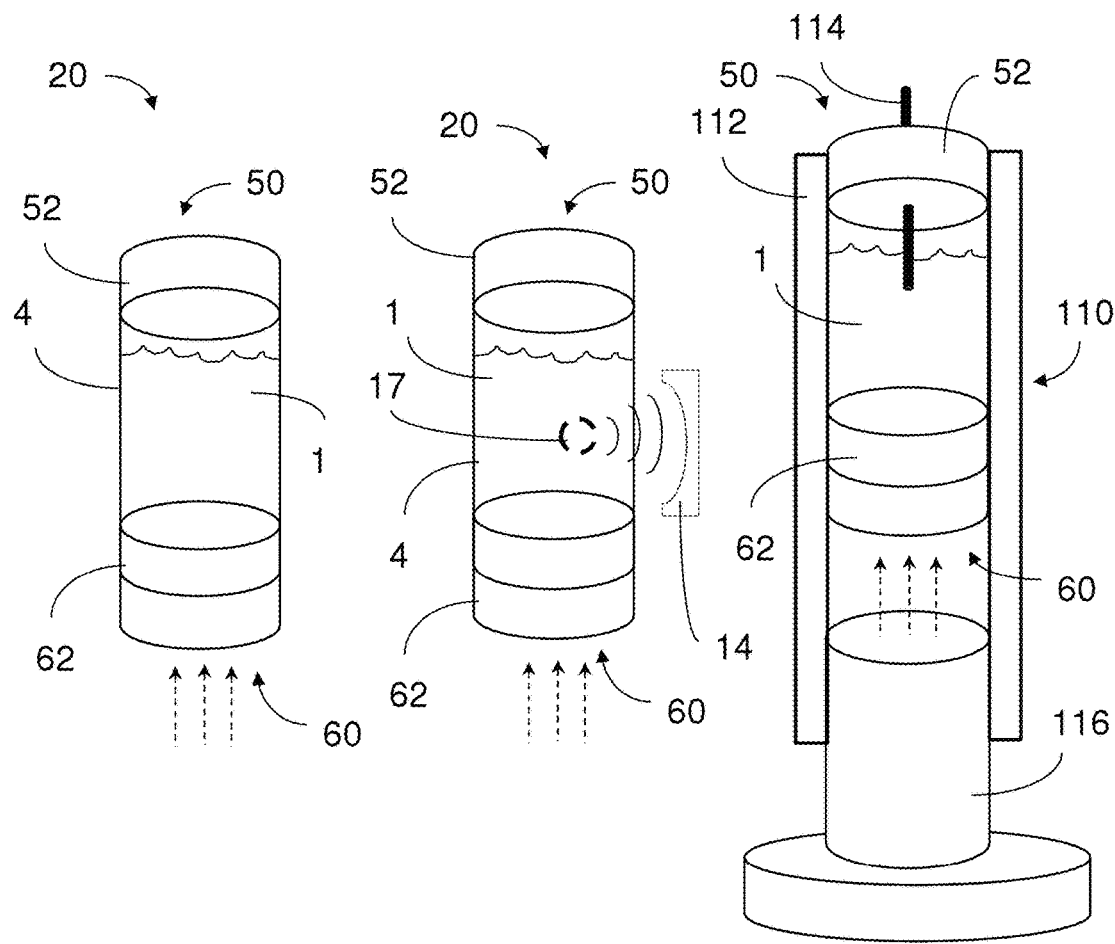

As discussed above, an appropriate amount of force may be applied to the plunger 62 in a direction toward the transfer end 50 may pressurize the interior space of the vessel and, hence, pressurization of the sample. FIG. 11 depicts dashed arrows signifying force applied to the plunger 62 so as to pressurize the sample to a pressure greater than that of the surrounding environment. As shown in FIG. 12, such overpressure of the sample may be applied and maintained during focused acoustic treatment of the sample from a transducer 14 spaced from and exterior to the vessel 4. Focused acoustic treatment of the sample when subject to overpressure may result in enhanced sterilization or other processing of the sample. In some embodiments, during focused acoustic treatment, the plunger 62 is urged toward the transfer end 50 so as to increase pressure of the sample while being processed. In other embodiments, during focused acoustic treatment, the plunger 62 is maintained at a particular position so that the pressure of the sample (e.g., overpressure) remains generally constant.

In addition to focused acoustic treatment of the sample subject to overpressure, FIG. 12 further depicts focused acoustic treatment of the sample having a reduced headspace. While overpressure and reduced headspace are independently advantageous in enhancing the sterilization effects of focused acoustics on a sample, a combined environment of overpressure and reduced headspace during focused acoustic processing may synergistically result in even more effective sterilization or other processing of the sample within the interior space of the vessel.

The vessel 4 may be subject to continuous sweeping of the focused acoustic field (e.g., lateral movement of the transducer 14 relative to the vessel) so that the sample is thoroughly exposed to the focused acoustic energy. Such an arrangement ensures that the sample is fully mixed and/or sterilized.

Upon sterilization or other suitable processing of the sample, focused acoustic processing may cease and the cartridge containing the sterilized sample is prepared for medical treatment purposes, e.g., injection into a patient. Thus, in some embodiments, the cartridge 20 is placed in an appropriate syringe 110, such as that shown in FIG. 7 or 13, for subsequent delivery of the sample.

FIG. 13 depicts the cartridge disposed within the chamber 112 of the syringe where the needle 114 has pierced the sealed cover 52 and the plunger 116 of the syringe is moved toward the transfer end 50 to apply force to the plunger 62 of the cartridge, as illustrated by the dashed arrows. As a result, the sample 1 within the vessel, sterilized through focused acoustics, may be delivered through the needle 114.

FIGS. 14-18 depict another illustrative embodiment of a process using a fluid delivery cartridge 20 to sterilize a sample 1 for subsequent medical treatment. In this embodiment, the sample comprises a solid material 2 and a liquid 3 that are to be mixed and/or sterilized using focused acoustics. Once sufficiently processed, the solid material 2 and liquid 3 combine to form the sample 1 (e.g., dissolved, reacted, etc.) that is subsequently used for medical treatment.

Figure 14:
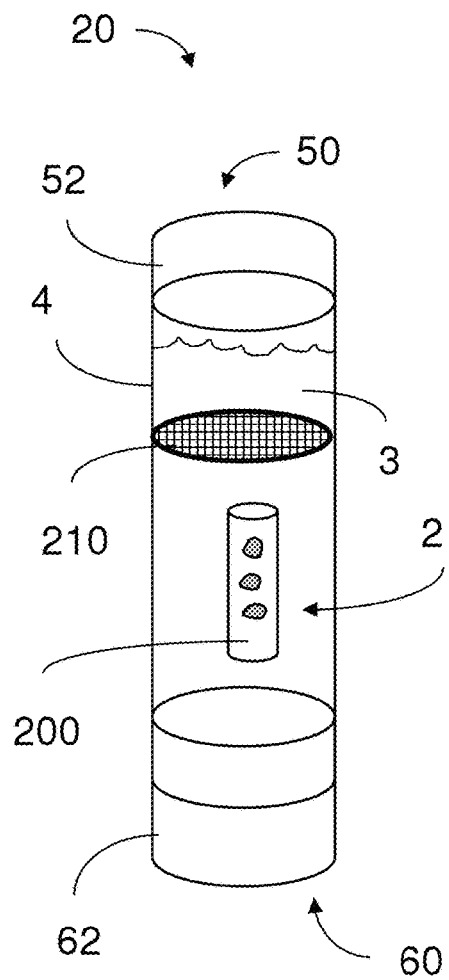

As shown in FIG. 14, a sealed capsule 200 (e.g., sterile bullet-shaped container) containing a solid material 2 (e.g., powder) is provided within the interior space of the vessel 4 along with a liquid 3 (e.g., saline, liquid carrier solution, etc.). The vessel may further include a filter 210, such as a mesh or other filtration arrangement. To mix the solid material 2 and the liquid 3, the sealed capsule 200 is broken into pieces 200a, 200b or otherwise opened, releasing and bringing the solid material 2 in contact with the liquid 3.

Figure 15:
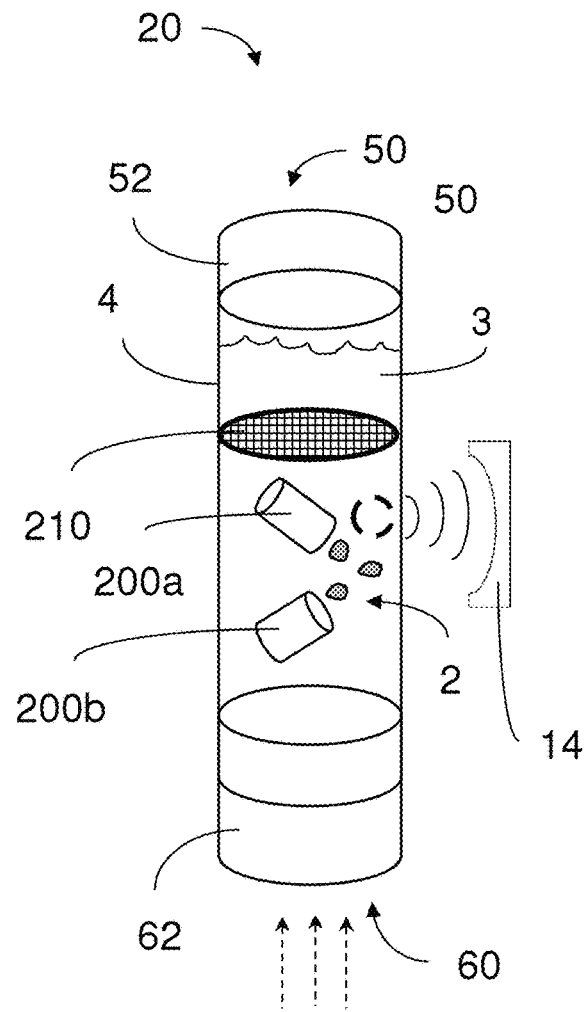

As shown in FIG. 15, the mixture of solid material 2 and liquid 3 is subjected to focused acoustic processing while also optionally being pressurized due to the application of a suitable amount of force from the plunger 62 at the plunger end 60. Accordingly, the solid material 2 becomes fully mixed and dissolved in the liquid 3 to form the sample 1 and may also be sterilized or otherwise processed in a manner sufficient to serve as a suitable payload for medical treatment.

As a result, as shown in FIG. 16, the solid material 2 and liquid 3 are suitably mixed and sterilized to form the sample 1 that will ultimately exit out of the vessel as a sterilized payload for delivery to a patient. While capsule pieces 200a, 200b (if present) remain within the vessel, the mesh 210 keeps the pieces contained within a portion of the vessel, preventing exit of the pieces from the cartridge during delivery.

FIG. 17 depicts the cartridge 20 disposed within the chamber 112 of a syringe 110. The needle 114 has pierced the sealed cover 52 and the plunger 116 is moved so as to force the plunger 62 of the vessel in a direction toward the transfer end 50, as shown by the dashed arrows. The filter 210 is provided within the vessel to prevent the broken capsule pieces 200a, 200b from entering into the needle 114, filtering the payload. As a result, the fully mixed and sterilized sample 1, comprising a sterilized payload of the solid material 2 dissolved in the liquid 3, within the vessel may be forced from the vessel and through the needle 114 for delivery.

In some embodiments, devices for sterilizing samples used for medical treatment under focused acoustics may incorporate a flow through arrangement. For example, a vessel having an interior space that is subject to overpressure and reduced headspace may have an inlet and an outlet through which sample fluid to be treated using focused acoustics may flow. Accordingly, a sample fluid flowing through a chamber that is optionally pressurized and/or with a reduced headspace may be sterilized with focused acoustic processing. Various systems and methods of flow through arrangements used in cooperation with focused acoustics are described in International Application No. PCT/US2011/058320, entitled "Systems for Acoustically Treating Material," which may be used in association with aspects of the present disclosure.

Figure 18:
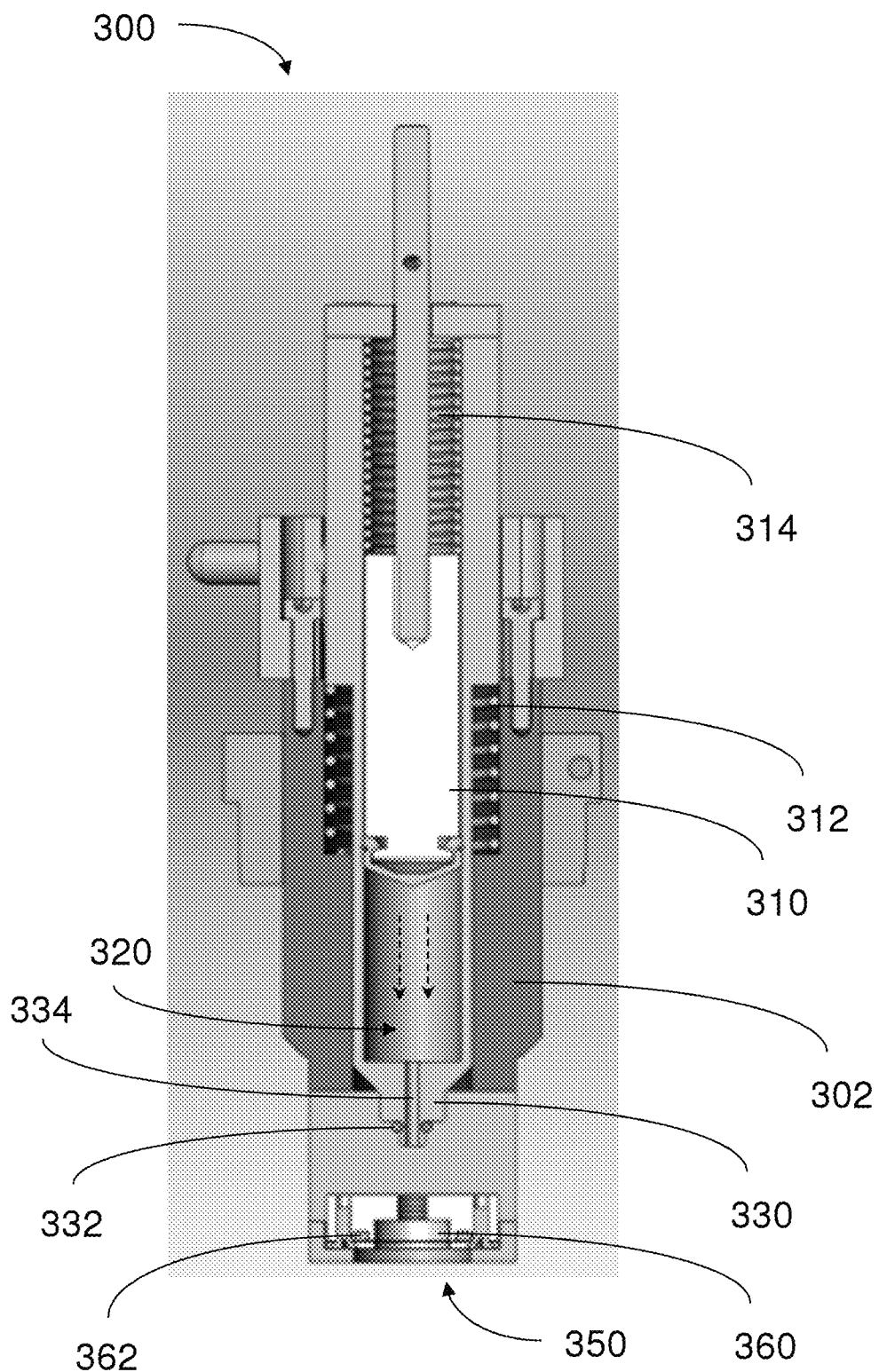
FIG. 18 depicts a pressurization device in accordance with some embodiments.

A vessel, cartridge, or any other device having a chamber may be pressurized by any suitable manner. In some embodiments, a spring-loaded device may engage with a chamber and provide a biasing force that effectively serves to pressurizes the chamber. FIG. 18 depicts an illustrative embodiment of a pressurizing device 300 that may be suitable to engage and provide pressure to a chamber 350 (not fully shown in FIG. 18), such as for sterilization or other processing of samples in cartridges for medical treatment described herein. FIG. 18 depicts a coupling member 360 of the chamber 350 that may be appropriately engaged with a coupling member 330 of the pressurizing device 300 (although the pressurizing device and the chamber are not shown to be connected to one another in the figure).

The device 300 includes a housing 302 for a piston 310 disposed within a piston chamber 320. Contained within the piston chamber 320 is air or an inert gas that may be ultimately used to pressurize the chamber 360 (e.g., vessel, cartridge). The piston 310 is attached to biasing members 312, 314 (e.g., springs) which provide separate biasing functions. The biasing member 312 serves to hold the piston chamber 320 of the pressurizing device 300 against the process chamber 350, compressing respective o-rings 332, 362 to create a sealed connection. Upon suitable connection, the biasing member 314 may be used to force the piston in a direction illustrated by the dashed arrows so that any gas or fluid contained within the piston chamber 320 is forced through a channel 334 and into the chamber 350, pressurizing the chamber 350.

In some embodiments, the pressurizing device 300 may be appropriate for providing pressure to a fluid delivery cartridge 20 where the device 300 and the cartridge are appropriately engaged through coupling members 330, 360 (e.g., via interference/friction fit, fasteners, adhesive, spring-loaded biasing force). For instance, once the interior space 31 of the vessel 4 of the cartridge 20 is hermetically sealed and the sample is injected into the interior space, the sample may be subjected to focused acoustic processing as well as an overpressure to enhance the focused acoustics. The pressurizing device 300 may be appropriately coupled to the cartridge 20. The biasing member 314 of the device 300 provides a biasing force on the piston 310 to move through the piston chamber 320 and force air/gas/fluid out the channel 334. In some embodiments, this air/gas/fluid may be transferred to the cartridge 20 as a force provided at the plunger end 60 to move the plunger 62 in a direction toward the transfer end 50, thereby pressurizing, or maintaining pressure of, the interior space of the vessel. Or, in other embodiments, the air/gas/fluid may be an inert gas that is transferred into the interior space 31 of the vessel 4, for example, through the transfer end 50 of the cartridge 20.

Figure 19:
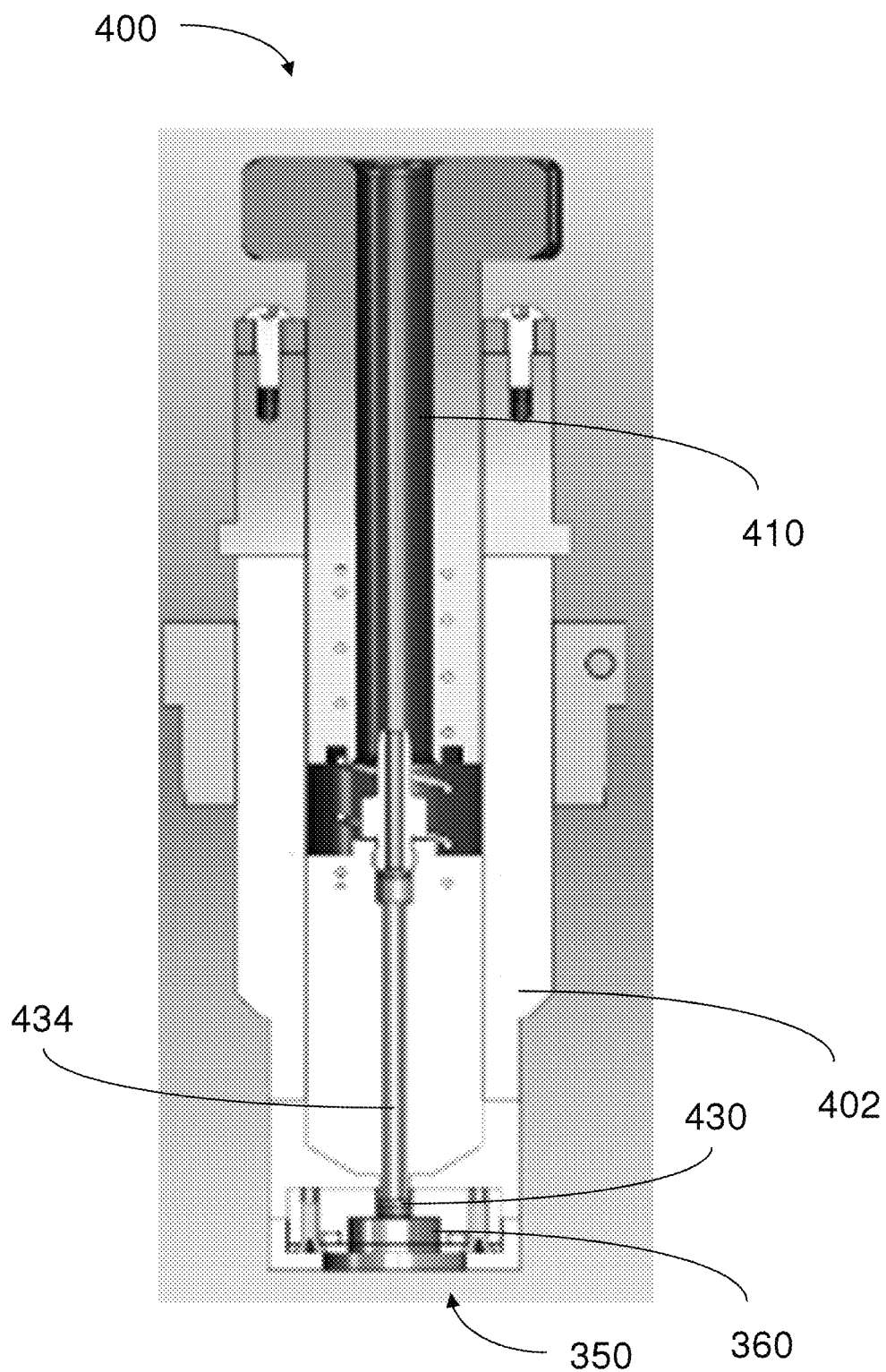
FIG. 19 illustrates another pressurization device in accordance with some embodiments.

In some embodiments, a gas-line device may engage with and pressurize the chamber. FIG. 19 depicts an illustrative embodiment of another pressurizing device 400 that may be suitable to engage and provide pressure to a chamber 350 useful for sterilization or other processing of samples in cartridges for medical treatment. FIG. 19 depicts a coupling member 360 of the chamber 350 that may be appropriately engaged with a coupling member 430 of the pressurizing device 400.

The device 400 includes a housing 402 for a chamber 410 through which gas may be forcibly injected through to pressurize the chamber 360 (e.g., vessel, cartridge). Upon suitable connection between the device 400 and the chamber 350, gas may be forced from the chamber 410 through a channel 434 and into the chamber 350, pressurizing the chamber 350. The pressurizing device 400 may be appropriate for providing pressure to a fluid delivery cartridge 20 where the device 400 and the cartridge are appropriately engaged through coupling members 430, 360 (e.g., via interference/friction fit, fasteners, adhesive, spring-loaded biasing force). For instance, when the interior space 31 of the vessel 4 of the cartridge 20 is hermetically sealed and the sample is injected into the interior space, the sample may be subjected to focused acoustic processing as well as an overpressure to enhance the focused acoustics.

In some embodiments, air/gas/fluid may be transferred to the cartridge 20 as a force provided at the plunger end 60 to move the plunger 62 in a direction toward the transfer end 50, thereby pressurizing, or maintaining pressure of, the interior space of the vessel. Or, in other embodiments, the air/gas/fluid may be an inert gas that is transferred into the interior space 31 of the vessel 4, for example, through the transfer end 50 of the cartridge 20.

In some embodiments, pressure may be applied to the sample or to the medium transmitting the acoustic energy, for example, by pressurizing the fluid, to improve acoustic coupling between the acoustic energy source and the sample. Or, the sample within an interior space of a vessel may be pressurized relative to standard atmospheric pressure (e.g., to 2, 3, 4, or more atmospheres of pressure) to improve sample processing. When focused acoustic energy is subsequently applied to the sample, the desired result may be obtained in a shorter time period and/or, in some applications, may also result in improved sample processing and output quality (e.g., a fully sterilized sample suitable for medical treatment). In certain embodiments, an air-tight seal is formed between the interior space of the vessel (e.g., a cover or other sealing material) to permit pressurization of the interior space of the vessel relative to the surrounding atmosphere.

In some cases, without wishing to be bound by theory, by increasing the pressure upon which the sample is subject, the acoustic energy dose required to cavitate portions of the sample (e.g., liquid, solution) may be effectively greater or otherwise enhanced. This may increase the shear forces consequent to cavitation bubble collapse. This may also result in greater retention time of the sample in the focal zone of the applied acoustic field and/or reduced rate of sample escaping the focal zone. This in turn may effectively increase the collision frequency of the sample with the acoustic bubbles generated by the applied energy and/or increase their resultant shear forces upon bubble collapse. In some cases, it is possible that pressurization of the sample during ultrasonic treatment may effect a transient increase in the effective viscosity of the sample, and that the acoustic energy has a greater effect in this altered state. This increase in effective strength may result in the observation of finer particle formation, faster tissue homogenization, accelerated lysis of microbial organisms, more effective sterilization of the sample, or otherwise provide for increased precision or speed of processing using the acoustic energy treatment process.

In some cases, acoustic treatment of a sample causes cavitation or other disruption in the sample such that energy that would otherwise be directed to processing sample material is absorbed, reflected or otherwise wasted or left unused for processing the sample. For example, cavitation or other relatively violent motion in a sample caused by acoustic energy can cause a portion of a sample to be ejected from the sample and into other areas of a vessel holding the sample, such as on the vessel sidewall. Time spent by the ejected sample portion outside of an acoustic focal zone or other area where the sample portion can be subjected to suitable acoustic energy may cause the sample to be incompletely or otherwise improperly processed or result in a process that requires more time and/or energy than necessary to achieve the desired result. Indeed, in some cases, ejected sample material may stick to a vessel sidewall or other location outside of the main sample volume, thus resulting in the ejected material not being acoustically processed at all.

In addition, the inventors have unexpectedly found that such acoustic energy loss or waste can be caused by gas present in the sample interfering with the acoustic energy. Thus, the inventors have discovered that acoustic energy loss or otherwise inefficient acoustic processing can be substantially minimized by reducing an amount of gas that can be absorbed, dissolved or otherwise enter into a liquid portion of a sample.

Without wishing to be bound to any particular theory, the inventors believe that acoustic processing of a sample that includes liquid, particularly at relatively higher energy levels, tends to disrupt the interface between the sample and a gas above the sample. This disruption, which in some cases may include turbulent motion at the interface, may cause transfer of gas into the sample liquid (e.g., such as by dissolution or other mechanism). Gas carried by the sample liquid (e.g., whether dissolved and/or in bubble form) may interfere with acoustic processing, such as by gas bubbles reflecting acoustic energy, an increase in gas bubbles present in the sample caused by release of dissolved gas from the liquid, increased pressure in collapsing cavitation bubbles reducing energy that would otherwise be directed to sample material, and/or potentially other mechanisms.

A headspace above a sample may be reduced in volume and/or a surface area presented to the sample. Reduction or other control of the headspace may in some arrangements provide the ability to reduce or eliminate ejection or other movement of sample material from a desired region in a vessel, may provide for more efficient transmission or use of acoustic energy in the sample material, or other features. For example, the inventors have found that reducing a headspace size for a sample (whether volume or surface area presented to a sample) can reduce the acoustic intensity or power and/or reduce processing time needed to achieve a desired result of the acoustic processing. For example, it has been found that processing of a 1.0 milliliter (ml) sample in the presence of a 0.9 ml headspace requires a power level of about 36 watts and a processing time of 60 minutes to cause a desired result (e.g., particle size reduction from 70 microns to 25 microns in this example). However, processing of a 1.9 ml sample volume of the same material (i.e., a larger volume) with a reduced headspace volume of less than 25 microliters at the same acoustic power level (e.g., 36 watts) has been found to achieve the same result in 15 minutes processing time.

In some cases, more efficient acoustic processing is believed to be provided by reducing an amount of gas that is dissolved or otherwise entrained in the sample. By reducing the amount of gas in the sample, less gas may be present in the sample to be released into bubbles that reflect acoustic energy and/or to interfere with cavitation bubble collapse, etc. As a result, reducing a headspace size may be effective in reducing gas entrained into a sample during acoustic processing, thereby making the acoustic processing more efficient or otherwise more effective.

The acoustic energy may be arranged in any suitable way, e.g., be sufficient to cause at least one of lysing, extraction, permeabilizing, stirring, catalyzing, degrading, fluidization, heating, particle breakdown, nucleic acid shearing, sterilization or disruption of molecular bonds in the sample. In some embodiments, the acoustic energy source is spaced from and exterior to the vessel, and the acoustic energy comprises a frequency of between about 100 kilohertz and about 100 megahertz and a focal zone having a width of less than about 2 centimeters, and wherein at least a portion of the acoustic energy is adapted to propagate exterior to the vessel.

In accordance with one aspect of the present disclosure, a retention time of a sample in an acoustic focal zone may be increased, e.g., by minimizing the gaseous headspace size in a processing vessel and/or controlling interaction between the sample and acoustic energy, thereby enabling higher acoustic doses to be delivered to the sample. As a result, sample processing time may be reduced, improving processing efficiency and target recovery.

In another aspect of the present disclosure, an efficiency of use of acoustic energy in a sample may be enhanced, e.g., by reducing an amount of gas that is entrained in the sample. In some embodiments, gas entrainment in a sample may be reduced by reducing or otherwise controlling a size of the headspace adjacent the sample. By reducing the volume and/or surface area of a headspace presented to a sample, an amount of gas available for entrainment into the sample can be reduced, or a rate at which the gas can be entrained may be reduced. This can help reduce bubble formation in the sample during acoustic treatment and/or interference of gas with cavitation bubble collapse, helping to increase an amount of acoustic energy that is used for treating the sample rather than being reflected out of the sample vessel or absorbed by increased cavitation bubble pressure.

In another aspect of the present disclosure, a processing volume or volume within which all or a portion of a sample is located for acoustic treatment, may be controlled in a vessel. For example, the gaseous headspace in a vessel may be reduced by positioning a wall, stop or other headspace control member in the vessel so that the headspace control member is located at or desirably near (e.g., above or below) a top surface of a sample in the vessel. The sample may be liquid, solid, a mixture of solid material in a liquid, or any other suitable arrangement. The vessel may take any suitable form as discussed above, such as a tube, well in a microtiter plate, a cube-shaped vessel, etc.

In another aspect of the present disclosure, a headspace control member may be arranged to present a rigid surface to the sample to reflect acoustic energy back toward the sample and/or a focal zone of the acoustic energy. In some arrangements, the rigid, acoustic energy reflecting surface may significantly improve the efficiency of acoustic processing. For example, it has been surprisingly found that a metal plate located at or near a sample interface may reduce a processing time by a factor of up to 10 (i.e., processing can be completed up to 10 times faster than a processing arrangement that is otherwise identical but does not include a rigid element presented to the sample). The rigid surface may be provided on a side of the sample that is opposite the acoustic source, e.g., so that acoustic energy is reflected by the rigid surface back toward the sample and the acoustic source.

Having thus described several aspects of at least one embodiment of the present disclosure, it is to be appreciated various alterations, modifications, and improvements will readily occur to those skilled in the art. Such alterations, modifications, and improvements are intended to be part of this disclosure, and are intended to be within the spirit and scope of the present disclosure. Accordingly, the foregoing description and drawings are by way of example only. It will be apparent that other embodiments and various modifications may be made to embodiments the present disclosure without departing from the scope thereof. The foregoing description is intended merely to be illustrative and not restrictive thereof. The scope of the present disclosure is defined by the appended claims and equivalents thereto.

The invention claimed is:

1. A method for using a fluid delivery cartridge, comprising:
    providing a fluid delivery cartridge having a vessel with a transfer end opposite a plunger end, the transfer end including a sealed cover that is pierceable, the vessel having a plunger movably disposed in the vessel and located adjacent the sealed cover;
    providing a liquid into the vessel by piercing the sealed cover and passing the liquid through the sealed cover and into the vessel;
    moving the plunger in the vessel in a direction away from the sealed cover and toward the plunger end to accommodate liquid provided into the vessel;
    associating the cartridge with a focused acoustic treatment system and exposing the liquid in the cartridge to focused acoustic energy to sterilize the liquid; and
    dispensing the sterilized liquid from the fluid delivery cartridge for delivery to a subject by piercing the sealed cover and moving the plunger toward the transfer end to force the sterilized liquid from the vessel.

2. The method of claim 1, wherein the vessel includes a cylindrical tube.

3. The method of claim 1, wherein the step of providing the liquid includes providing the liquid under pressure into the vessel sufficient to move the plunger toward the plunger end.

4. The method of claim 1, further comprising completing liquid delivery into the vessel such that a volume of gas in the vessel is less than 10% of a volume of liquid in the vessel.

5. The method of claim 1, further comprising completing liquid delivery into the vessel such that a volume of liquid in the vessel is less than approximately 2 mL.

6. The method of claim 1, wherein the step of dispensing includes associating the cartridge with a syringe having a needle and arranged to pierce the sealed cover and move the plunger toward the transfer end to deliver liquid in the cartridge to the needle.

7. The method of claim 1, wherein the step of providing a fluid delivery cartridge includes providing a powder in the vessel.

8. The method of claim 7, wherein the powder is contained in a sealed capsule in the vessel.

9. The method of claim 8, further comprising opening the sealed capsule to expose the powder to the liquid.

10. A fluid delivery cartridge, comprising:
    a vessel having a transfer end opposite a plunger end;
    a sealed cover that is pierceable attached at the transfer end; and
    a plunger movably disposed in the vessel and located adjacent the sealed cover, the plunger arranged for movement in the vessel in a direction away from the sealed cover and toward the plunger end with introduction of liquid into the vessel by piercing the sealed cover and passing the liquid through the pierced sealed cover,
    wherein the fluid delivery cartridge is arranged for association with a focused acoustic treatment system and exposure to focused acoustic energy to sterilize liquid in the vessel, and the fluid delivery cartridge is arranged for dispensing the sterilized liquid from the fluid delivery cartridge for delivery to a subject by piercing the sealed cover and moving the plunger toward the transfer end to force the sterilized liquid from the vessel.

11. The cartridge of claim 10, wherein the sealed cover includes a cap crimped to the vessel at the transfer end and a pierceable membrane positioned between the crimped cap and the vessel.

12. The cartridge of claim 10, wherein the sealed cover includes a pierceable plug made of a resilient material.

13. A method for processing a drug in a fluid delivery cartridge, comprising:
    providing a fluid delivery cartridge having a vessel with a transfer end opposite a plunger end, the transfer end including a sealed cover that is pierceable, the vessel having a plunger movably disposed in the vessel;
    providing a liquid into the vessel by piercing the sealed cover, passing the liquid through the sealed cover and into the vessel under pressure sufficient to move the plunger away from the transfer end and toward the plunger end to accommodate liquid provided into the vessel, the liquid forming at least part of a payload in the vessel;
    exposing the fluid delivery cartridge to focused acoustic energy to process the payload, processing of the payload including exposing the payload to acoustic energy suitable to at least mix or sterilize the payload; and
    dispensing the acoustic energy-processed payload from the fluid delivery cartridge for delivery to a subject by piercing the sealed cover and moving the plunger toward the transfer end to force the payload from the vessel.

14. The method of claim 13, wherein the exposing step includes exposing the payload to acoustic energy suitable to sterilize the payload.

15. The method of claim 13, wherein the payload includes a powder and a liquid, and exposing step includes exposing the payload to acoustic energy suitable to mix the powder and liquid of the payload.

16. The method of claim 15, wherein the payload includes a capsule containing the powder and the capsule is positioned in the vessel.

17. The method of claim 16, further comprising opening the capsule to release the powder from the capsule for contact with the liquid.

18. The method of claim 13, wherein the step of dispensing comprises associating the cartridge with a syringe having a needle and arranged to pierce the sealed cover and move the plunger toward the transfer end to deliver liquid in the cartridge to the needle.

19. The method of claim 13, wherein the exposing step includes applying force to the plunger to urge the plunger to move toward the transfer end and pressurize the payload while exposing the payload to acoustic energy.

20. The method of claim 13, further comprising completing liquid delivery into the vessel such that a volume of gas in the vessel is less than 10% of a volume of liquid in the vessel.

* * * * *